(12) United States Patent
Madabhushi et al.

(10) Patent No.: US 11,922,625 B2
(45) Date of Patent: Mar. 5, 2024

(54) PREDICTING OVERALL SURVIVAL IN EARLY STAGE LUNG CANCER WITH FEATURE DRIVEN LOCAL CELL GRAPHS (FEDEG)

(71) Applicant: Case Western Reserve University, Cleveland, OH (US)

(72) Inventors: Anant Madabhushi, Shaker Heights, OH (US); Cheng Lu, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 17/896,454

(22) Filed: Aug. 26, 2022

(65) Prior Publication Data
US 2022/0405931 A1 Dec. 22, 2022

Related U.S. Application Data

(63) Continuation of application No. 16/265,068, filed on Feb. 1, 2019, now Pat. No. 11,455,718.
(Continued)

(51) Int. Cl.
*G06K 9/00* (2022.01)
*G06T 7/00* (2017.01)
(Continued)

(52) U.S. Cl.
CPC .......... *G06T 7/0012* (2013.01); *G06V 20/698* (2022.01); *G16B 40/00* (2019.02);
(Continued)

(58) Field of Classification Search
None
See application file for complete search history.

(56) References Cited

U.S. PATENT DOCUMENTS 10,503,959 B2  12/2019  Madabhushi et al.
10,783,627 B2   9/2020  Madabhushi et al.
(Continued)

OTHER PUBLICATIONS

Ali et al. "Cell cluster graph for prediction of biochemical recurrence in prostate cancer patients from tissue microarrays" (Year: 2013).*

(Continued)

*Primary Examiner* — Soo Jin Park
(74) *Attorney, Agent, or Firm* — Eschweiler & Potashnik

(57) ABSTRACT

Embodiments include accessing an image of a region of tissue demonstrating cancerous pathology; detecting a plurality of cells represented in the image; segmenting a cellular nucleus of a first member of the plurality of cells and a cellular nucleus of at least one second, different member of the plurality of cells; extracting a set of nuclear morphology features from the plurality of cells; constructing a feature driven local cell graph (FeDeG) based on the set of nuclear morphology features and a spatial relationship between the cellular nuclei using a mean-shift clustering approach; computing a set of FeDeG features based on the FeDeG; providing the FeDeG features to a machine learning classifier; receiving, from the machine learning classifier, a classification of the region of tissue as a long-term or a short-term survivor, based, at least in part, on the set of FeDeG features; and displaying the classification.

20 Claims, 10 Drawing Sheets

Related U.S. Application Data

(60) Provisional application No. 62/640,701, filed on Mar. 9, 2018.

(51) Int. Cl.
 *G06V 20/69* (2022.01)
 *G16B 40/00* (2019.01)

(52) U.S. Cl.
 CPC ............... *G06T 2207/10056* (2013.01); *G06T 2207/20081* (2013.01); *G06T 2207/30024* (2013.01); *G06T 2207/30061* (2013.01); *G06T 2207/30096* (2013.01)

(56) References Cited

U.S. PATENT DOCUMENTS

2015/0254494 A1* 9/2015 Madabhushi ......... G06T 7/0012
 382/133
2017/0193657 A1* 7/2017 Madabhushi ..... G06F 18/24317

OTHER PUBLICATIONS

Wang et al., "Prediction of recurrence in early stage on-small cell lung cancer using computer extracted nuclear features from digital h&e images" (Year: 2017).*

Shen et al., "Segmenting multiple overlapping nuclei in h&e stained breast cancer histopathology images based on an improved watershed" (Year: 2015).*

Lu et al., "Multi-pass adaptive voting for nuclei detection in histopathological images", Oct. 2016 (Year: 2016).*

Wang et al., "Prediction of recurrence in early stage non-small cell lung cancer using computer extracted nuclear features from digital H&E images" (Year: 2017).

Lee et al. ("Nuclear shape and architecture in benign fields predict biochemical recurrence in prostate cancer patients following radical prostatectomy: preliminary findings") (Year: 2017).

Notice of Allowance dated May 4, 2022 for U.S. Appl. No. 16/265,068.

* cited by examiner

PREDICTING OVERALL SURVIVAL IN EARLY STAGE LUNG CANCER WITH FEATURE DRIVEN LOCAL CELL GRAPHS (FEDEG)

CROSS REFERENCE TO RELATED APPLICATIONS

This Application is a Continuation of U.S. application Ser. No. 16/265,068, filed on Feb. 1, 2019, which claims the benefit of U.S. Provisional Application No. 62/640,701, filed on Mar. 9, 2018. The contents of the above-reference Patent Applications are hereby incorporated by reference in their entirety.

Federal Funding Notice

This invention was made with government support under the grant(s) 1U24CA199374-01, R01 CA202752-01A1, R01 CA208236-01A1, R01 CA216579-01A1, and R01 CA220581-01A1 awarded by the National Institutes of Health. Also W81XWH-18-1-0440 awarded by the Department of Defense. The government has certain rights in the invention.

BACKGROUND

The local arrangement of nuclei in histopathology images may have prognostic value in the context of different cancers. To capture the local nuclear architecture information, local cell cluster graph based measurements may be employed. However, existing approaches to constructing cell graphs that only utilize nuclear spatial proximity do not differentiate between different cell types when constructing cell graphs. Thus, a local cell graph construction approach that discriminates between different cell populations would be advantageous.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Changes in distribution, appearance, size, morphology, and arrangement of histologic primitives, including nuclei or glands, may be predictive of tumor aggressiveness. In the context of lung cancer, more and less aggressive diseases are characterized by differences in nuclear shape, morphology, and arrangement. For different types of cancer, the hallmark of presence of disease is the disruption of architecture between nuclei and other primitives belonging to the same family (e.g., nuclei or lymphocytes). Conversely, aggressive tumors tend to exhibit lower degrees of structure and organization between the same class of primitives compared to less aggressive cancers.

Computational graph-based approaches may characterize spatial arrangement of nuclei in histopathology images to predict patient outcomes. Some existing approaches are based on global graphs, including Voronoi and Delaunay triangulation strategies that connect individual nuclei (representing graph vertices or nodes). These existing approaches then compute statistics relating to edge length and node density, and associate those statistics with disease outcome. Cell cluster graphs (CCG) in which nodes are defined on groups or clusters of nuclei rather than in individual nuclei, may be prognostic. However, the graph connections of existing approaches that focus solely on cell proximity do not discriminate between different cell populations. For example, in existing approaches, the graph connections do not take into account whether the proximal cells are all cancer cells, or whether they belong to other families such as lymphocytes.

Figure 1:
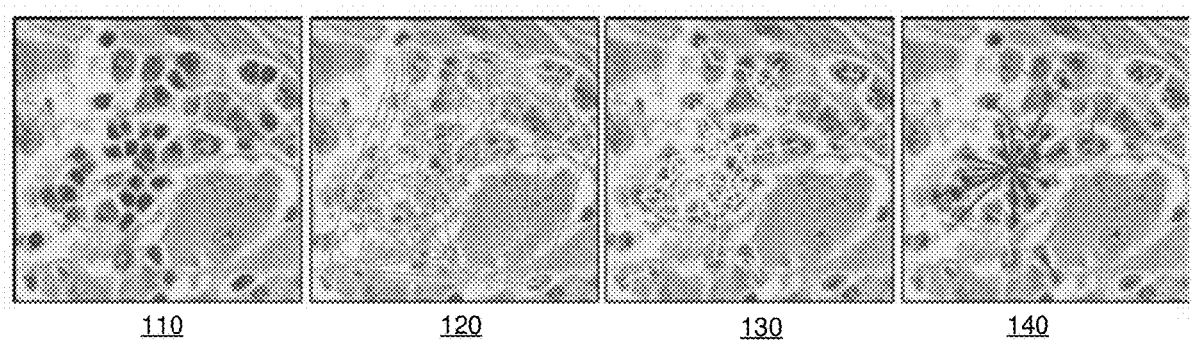
FIG. 1 illustrates local cell graphs.

Embodiments construct a feature driven local cell graph (FeDeG) based on spatial proximity and nuclear features of cellular nuclei in a region of tissue demonstrating early stage non-small cell lung cancer (NSCLC). Embodiments construct FeDeGs that comprise locally packed cell graphs that include nuclei with similar phenotype. FIG. 1 illustrates a hematoxylin and eosin (H&E) stained histology image 110 of a region of tissue demonstrating NSCLC. Histology image 110 includes lymphocytes and cancer cells. FIG. 1 also illustrates a global cell graph 120, overlaid on the same region of tissue represented in H&E stained histology image 110. In this example, the global cell graph 120 is a Delaunay triangulation-based graph. The global cell graph 120 connects all the nuclei in histology image 110, and does not capture local tumor morphology efficiently. FIG. 1 also illustrates, at 130, a cell cluster graph (CCG) based solely on the proximity of nuclei, overlaid on the same region of tissue represented in H&E stained histology image 110. The CCG illustrated at 130 only considers nuclear locations, which results in connecting lymphocytes and cancer cellular nuclei into a graph, which leaves important information involving local spatial interaction between different cellular clusters unexploited. FIG. 1 further illustrates, at 140, FeDeG driven by nuclear intensity and spatial proximity of nuclei, overlaid on the same region of tissue represented in H&E stained histology image 110. The FeDeG illustrated at 140 incorporates a nuclear morphologic feature (i.e., nuclear mean intensity) into the graph construction process, which facilitates examining the interaction between different graphs of different cell types, and further reveals sub-visual information not visible to the human eye, from the underlying tissue.

Embodiments further compute quantitative histomorphometric features based on the FeDeG. Embodiments compute features that quantify intersection between different FeDeGs, size of FeDeGs, disorder of nuclear morphology within a FeDeG, and spatial arrangement of FeDeGs. The quantitative histomorphometric features extracted by embodiments from FeDeGs differ from existing features extracted from CCGs or global graph-based approaches, which only quantify the density of local or global graphs, or the local or global distances between cells. Rather, the quantitative histomorphometric features extracted by embodiments from FeDeGs capture the interactions between and within local cell clusters with similar morphological properties.

Embodiments employ the FeDeGs and associated quantitative histomorphometric features in conjunction with a linear machine learning classifier to predict overall survival in early stage NSCLC. In existing approaches that employ machine learning classifiers to predict recurrence or overall survival in NSCLC using global architecture and nuclear shape features, the interactions between different local cell clusters are not explored. In contrast, embodiments classify the region of tissue demonstrating NSCLC using quantitative histomorphometric features that consider both spatial attributes and nuclear phenotype as input to the machine learning classifier.

Figure 2:
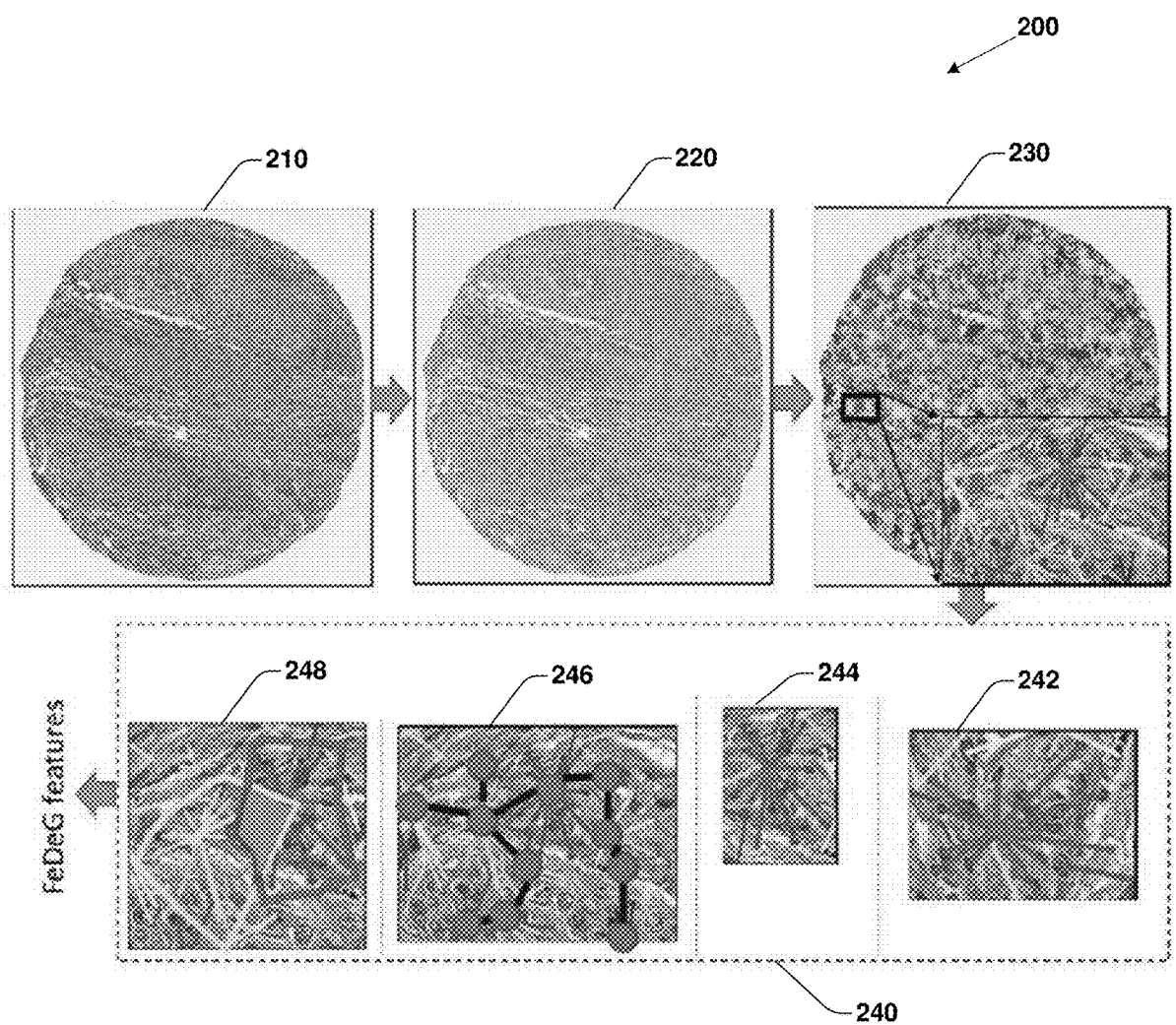
FIG. 2 illustrates a workflow for computing feature driven local cell graph (FeDeG) features.

An example embodiment is now described in more detail. FIG. 2 illustrates a flowchart of an exemplary workflow for FeDeG construction and associated FeDeG feature computation. In this embodiment at, 210, a histology image of a region of tissue demonstrating early stage NSCLC is accessed. The histology image includes a plurality of cellular nuclei. The plurality of cellular nuclei includes different types of cellular nuclei, including cancer cell nuclei, lymphocytes, or other types of nuclei.

In this embodiment, cellular nuclei represented in the histology image are segmented. Boundaries of segmented cellular nuclei are illustrated at 220. Embodiments may detect cells using a multiple-pass adaptive voting approach. Embodiments may employ a local optimal thresholding approach to segment nuclei from surrounding tissue by analyzing morphological features of the nuclei, including but not limited to, nuclear shape and nuclear area. In one embodiment, a set of six nuclear morphology features that describe the nuclear shape, size, and texture are computed for a segmented nuclei.

In this embodiment, at 230, FeDeG are constructed based, at least in part, on the nuclear morphology features. In the example illustrated at 230, the nuclear morphology feature includes a mean intensity of nuclei, while in another example, other features may be employed. In this embodiment, spatial and morphological features of nuclei are used for feature space analysis to construct a FeDeG. In this embodiment, feature space analysis to construct sub-graphs employs mean-shift clustering. Mean-shift clustering includes estimating the modes (i.e., stationary points of the density of nuclear morphology feature) of the underlying density function of the nuclear morphology feature. Mean-shift clustering then includes grouping nuclei into different sub-graphs based on the corresponding modes.

In one embodiment, N denotes the total number of nuclei in the image, and each nucleus has a corresponding feature vector in d-dimensional Euclidean space $R^d$, so that we have a set of nuclear feature vectors $X=x_1, x_1, \ldots, x_N$, where $x_n \in R^d$. For each feature vector $x_n \in X$ there is a corresponding mode $y_i$. The mode $y_i$ is initialized with the original feature vector $x_n$, i.e., $y_i^0=x_n$. The $y_i^u$ is then recursively updated, based on the neighborhood nuclear characteristics, using the following equation:

$$y_i^{u+1}=y_i^u+m_G(y_i^u), \quad 1 \le i \le n \qquad \text{(Eq. 1)}$$

where $y_i^{u+1}$ is the updated version of $y_i^u$. The vector $m_G(y_i^u)$ is called the mean-shift vector and calculates the difference between the weighted mean and the center of the kernel. The mean-shift vector always points toward the direction of maximum increase in the underlying density function. At the final step, each nuclear feature vector $x_n$ finds a corresponding mode $y_i$ which will be used for constructing the FeDeG.

Embodiments employ a Q-dimensional feature space which includes 2-D spatial coordinates (i.e., centroid location) of nuclei in the image and Q-2 of the nuclear morphologic features. These features are chosen based on the observation that the same types of nuclei are usually located closely together and have a similar phenotype. The corresponding multivariate kernel is defined as the product of two radially symmetric kernels as follows:

$$K_{h_s,h_m}(x_i) = \frac{C}{h_s^2 h_m^{Q-2}} k\left(\left\|\frac{x_{i,s}}{h_s}\right\|\right) k\left(\left\|\frac{x_{i,m}}{h_m}\right\|\right) \qquad \text{(Eq. 2)}$$

where $k(\cdot)$ is the profile of the kernel, $x_s$ is the spatial component, $x_m$ is the nuclear morphologic component, C is the normalization constant, and $h_s$ and $h_m$ are the kernel bandwidths controlling the size of the kernels. The higher value of the kernel bandwidths $h_s$ and $h_m$ correspond to more neighboring data points that are used to estimate the density in the Q-D feature space. This can be seen at 230 in FIG. 2, in which the FeDeGs were constructed in a 3-D feature space, i.e., the spatial x- and y-coordinates, and the nuclear intensity.

In this embodiment, quantitative histomorphometric FeDeG features are computed at 240. Based on the FeDeGs constructed at 230, embodiments derive four groups of quantitative histomorphometric FeDeG features. In this embodiment, the four groups of quantitative histomorphometric FeDeG features include an intersection between different FeDeGs feature group, a size of FeDeG feature group, a disorder of nuclear morphology feature group, and an architectural measures of FeDeG feature group. These quantitative histomorphometric features measure the interaction between FeDeGs, as well as the spatial arrangement of FeDeGs. A disorder of nuclear morphology with a FeDeG feature is illustrated at 242. A size of a FeDeG feature is illustrated at 244. In this embodiment, the number of cells in the FeDeG illustrated at 244 is thirteen, and the size of the FeDeG is computed as the number of cells divided by the area of the FeDeG. Architectural measures of FeDeGs are illustrated at 246. An intersection between different FeDeGs feature is illustrated at 248.

In one embodiment, the intersection between different FeDeGs feature group includes 44 features, including a portion or number of intersected FeDeGs feature, and a mean intersected area feature. The intersection between different FeDeGs group features quantify the interaction between local cell clusters. A larger portion of overlapped regions reflects a higher degree of inter-play between cell graphs with different phenotypes. For example, a large portion of overlapped regions between cancer cells and lymphocytes in NSCLC may indicate a better prognosis since there is more interplay between immune cells and cancer cells.

In one embodiment, the size of FeDeG feature group includes twelve features, including a size of FeDeG feature, and a number of cells in a FeDeG feature. The size of FeDeG features quantify the size of local cell clusters. The size of FeDeG reflects the local density of the nuclei with similar phenotypes, and thus indicates the morphology of the tumor in the local region.

In one embodiment, the disorder of nuclear morphology feature group includes eighteen features, including a variations of morphology within a FeDeG feature. The disorder of nuclear morphology features quantify disorder of nuclear morphology locally, by comparing the subtle morphological differences between all the nuclei within the FeDeG and the mean morphology feature of the underlying FeDeG. Higher disorder of the nuclear morphology within one FeDeG, for example, indicates more heterogeneity of the morphology in that local region.

In one embodiment, the architectural measures of FeDeGs feature group includes 102 features, including a global graph measurements feature. The architectural measures of FeDeGs features quantify the global architecture of FeDeGs. The architectural measures of FeDeGs feature group facilitates quantification of the global arrangement or distribution of cell clusters with similar appearance. The architectural measures of FeDeGs feature group includes a set of architectural measures at nuclei cluster level compared to the traditional global architecture measures used by existing approaches, which are at a nuclei level.

In one embodiment, an early stage NSCLC cohort including a total of 434 patients was accessed. Imagery in the form of digitized TMA images (scanned at 20× magnification digitally) corresponding to each member of the cohort, respectively, was accessed. Long term clinical out-come was available for all patients in this cohort (collected between 2004 and 2014), which resulted in two-hundred and eighty (280) short-term survival patients (less than 5 years after surgery) and 154 long-term survival patients (greater than 5 years after surgery).

In this embodiment, a FeDeG feature set including one-hundred and seventy six (176) FeDeG features describing the interaction between local cell clusters comprising nuclei with similar properties was generated. A linear discriminant analysis classifier (LDA) was trained based on the patient labels for samples, under 10-fold cross-validation (CV) with 100 runs. Within each fold, the top 10 predictive features were selected by using a Wilcoxon rank sum test (WRST). In embodiments, features that quantify measures of the degree of FeDeGs inter-section, and the variance of FeDeG graph sizes, were the two most frequently selected features by WRST across 100 runs of 10-fold cross-validation.

Figure 3:
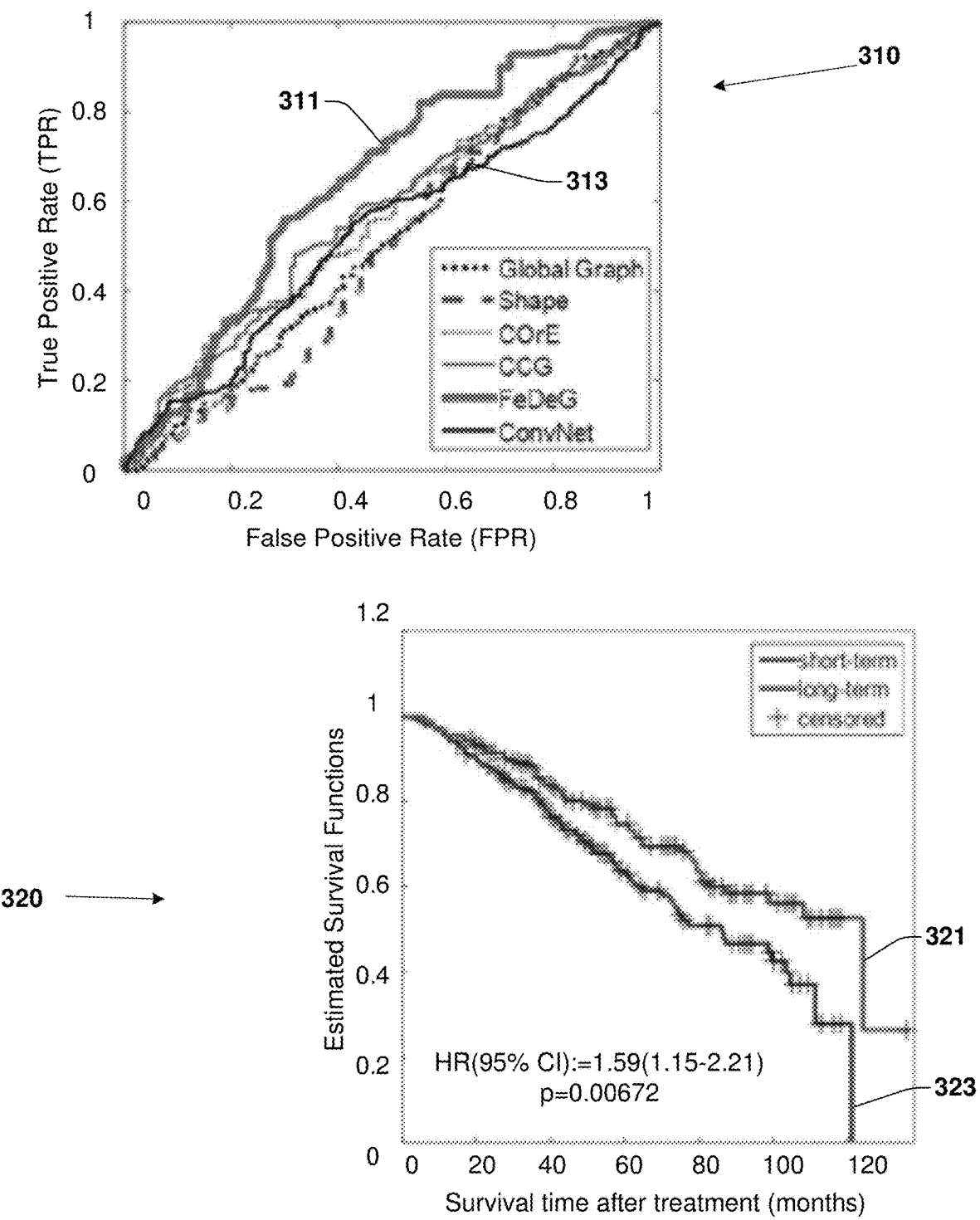
FIG. 3 illustrates receiver operating characteristic (ROC) curves in distinguishing short-term versus long-term survival.

FIG. 3 illustrates classification performance of embodiments compared with classification performance of existing approaches based on different types of feature sets. For each existing approach used for comparison with embodiments, an LDA was trained based on the patient labels for samples, under 10-fold CV with 100 runs. Within each fold, the top 10 predictive features were selected by using a WRST. The FeDeG based classifier according to embodiments described herein achieved the highest AUC of 0.68±0.02, outperforming the existing approaches. Embodiments classify tissue more accurately than existing histomorphometric based approaches involving description of cell morphology and architecture. Existing approaches were tested using the same segmentation approach as embodiments, on the same dataset, to calculate the nuclear boundaries and centroids. In particular, embodiments classify tissue more accurately than an existing approach that uses 100 features describing nuclear shape, an existing approach that uses 51 features describing global cell architectures, an existing approach that uses 24 features describing cell orientation entropy by COrE, and an existing approach that uses 35 CCG features describing local cell cluster arrangement. Embodiments further outperform an existing deep learning classifier. The existing deep learning classifier was implemented using the Alexnet style Convolutional Neural Network (CNN). Specifically, a 10-layer CNN architecture comprising 1 input layer, 5 convolution layers, 3 fully connected layers and 1 output layer was constructed. The input layer accepts an image patch of 256×256 pixels, and the out-put layer is a soft-max function which outputs the class probability of being positive or negative. In the DLM (i.e., the CNN), we split each TMA spot image into smaller patches of 200×200 pixels, the class labels for these image patches being assigned the same class label as that of the corresponding TMA spot image it was derived from. The average image size of the TMA spot was 3000×3000 pixels at 20× magnification, which in turn resulted in a total number of about 68,000 patches after filtering out unusable patches. The training and testing of the CNN was performed using a 10-fold cross-validation approach across each fold, all training and testing being done at the patient and not at the individual image-level. Once each of the individual image patches corresponding to a single patient has been assigned a class label, majority voting was employed to aggregate all the individual predictions to generate a patient-level prediction.

The global graph, shape, COrE, CCG, and DL (e.g., CNN) feature classifiers yielded AUCs of 0.56±0.02, 0.54±0.03, 0.61±0.02, 0.62±0.03, and 0.55±0.04, respectively. The receiver operating characteristic (ROC) curves are illustrated in FIG. 3 by graph 310. The ROC curve for embodiments is illustrated at 311. The ROCs for existing approaches are illustrated at 313. FIG. 3 further illustrates, at 320, Kaplan-Meier curves 321 and 323 associated with long-term and short-term survivors, respectively, for embodiments computed under a leave-one-out framework with p=0.00772, HR (95% CI)=1.59(1.15-2.21). The classification results demonstrate that in embodiments, locally extracted nuclear FeDeG features provide better prognostic value than those associated with global architecture. Comparing the performance of CCG and FeDeG based classifiers suggests that the organization of local cell clusters, where cluster membership was defined not solely based off spatial proximity but also on morphologic similarity, results in more highly prognostic signatures.

Figure 4:
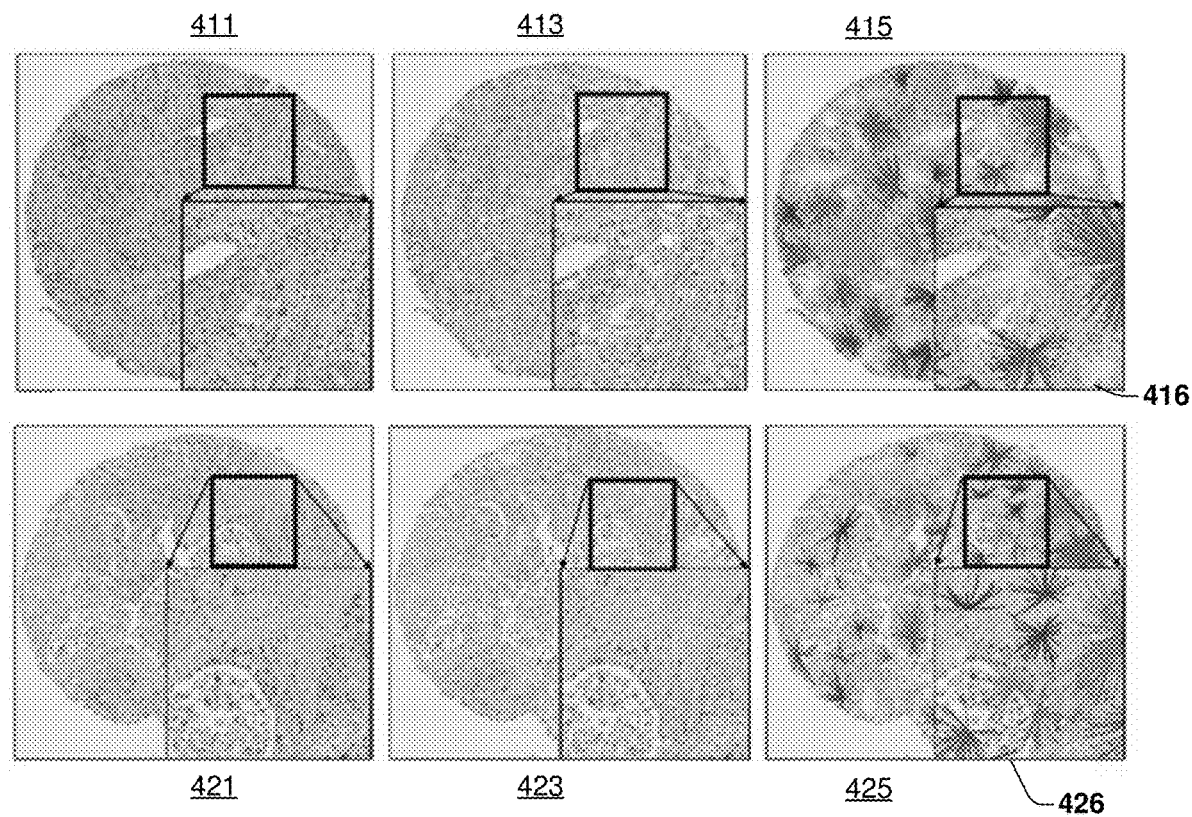
FIG. 4 illustrates regions of tissue demonstrating short-term and long-term survival.

FIG. 4 illustrates two representative H&E stained TMA spot images 411 and 421 of tissue demonstrating NSCLC. TMA spot image 411 is of a long-term survivor, and TMA spot image 421 is of a short-term survivor. FIG. 4 also illustrates the corresponding CCG feature representations at for the long-term survivor at 413 and the short-term survivor at 423. FIG. 4 further illustrates the FeDeG feature representations for the long-term survivor at 415 and the short term survivor at 425. The panel insets at 416 and 426 reveal the grouping discovered by the FeDeG of the TIL and cancer nuclei as distinct clusters with the associated spatial interaction between these two cell families, unlike the CCG representations at 413 and 423 which do not distinguish between the nuclei and TILs.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 5:
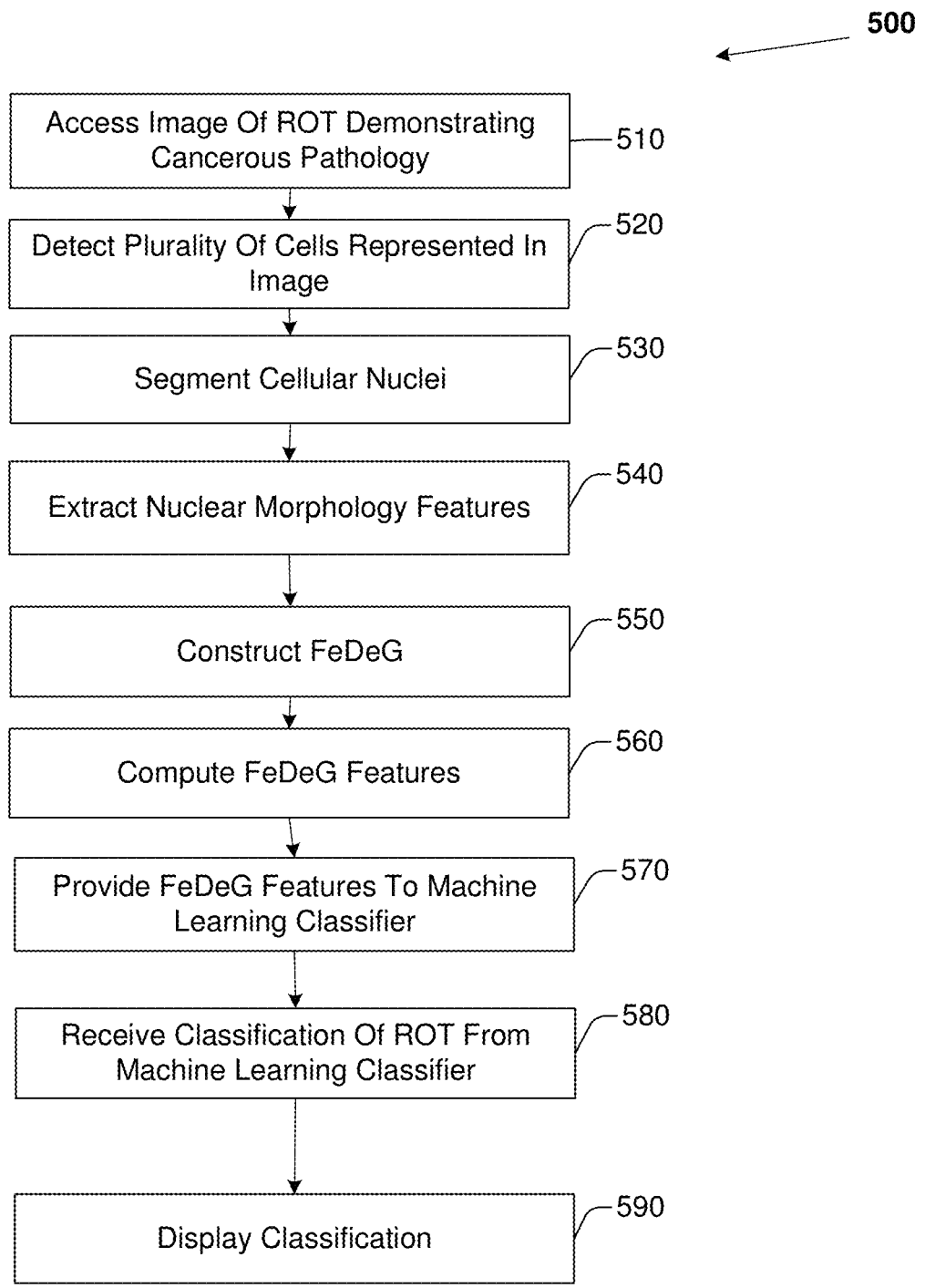
FIG. 5 is a flow diagram of example operations for predicting overall survival in non-small cell lung cancer (NSCLC).

FIG. 5 is a flow diagram of example operations 500 that may be performed by a processor for predicting overall survival in early stage lung cancer. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 500 includes, at 510, accessing an image of a region of tissue (ROT) demonstrating cancerous pathology. The image has a plurality of pixels, a pixel having an intensity. Accessing the image includes acquiring electronic data, reading from a computer file, receiving a computer file, reading from a computer memory, or other computerized activity not practically performed in a human mind. In one embodiment, the image is a digitized image of an H&E stained tissue micro array (TMA) image of a region of tissue demonstrating NSCLC. In one embodiment, the image is scanned at 20× magnification. In another embodiment, the image has other, different imaging parameters. While H&E stained images are described in this example, images having other stain types may be employed.

The set of operations 500 also includes, at 520 detecting a plurality of cells represented in the image. In one embodiment, detecting a plurality of cells represented in the image includes detecting the plurality of cells using a multiple-pass adaptive voting approach. In another embodiment, other cell detection techniques, including template matching or Laplacian of Gaussian filtering techniques may be employed. Detecting the plurality of cells includes acquiring electronic data, reading from a computer file, receiving a computer file, reading from a computer memory, or other computerized activity not practically performed in a human mind.

The set of operations 500 also includes, at 530, segmenting a cellular nucleus of a member of the plurality of cells. In one embodiment, segmenting a cellular nucleus includes segmenting the cellular nucleus using a local optimal thresholding approach. The local optimal thresholding approach is based on a cellular shape of the member of the plurality of cells, and a cellular area of the member of the plurality of cells. Segmenting a cellular nucleus includes acquiring electronic data, reading from a computer file, receiving a computer file, reading from a computer memory, or other computerized activity not practically performed in a human mind. In one embodiment, segmenting a cellular nucleus of a member of the plurality of cells includes segmenting a cellular nucleus of each member of the plurality of cells. In another embodiment, segmenting a cellular nucleus includes segmenting a cellular nucleus of a threshold number of members of the plurality of cells, for example, 75%, or 90%. Segmenting a cellular nucleus may include segmenting a cellular nucleus of a first member of the plurality of cells and a cellular nucleus of at least one second, different member of the plurality of cells.

The set of operations 500 also includes, at 540, extracting a set of nuclear morphology features from the segmented cellular nucleus. In one embodiment, nuclear morphology features may be extracted from a segmented cellular nucleus of each member of the plurality of cells, respectively. In one embodiment, nuclear morphology features may be extracted from a segmented cellular nucleus of a first member of the plurality of cells and the cellular nucleus of at least one second, different member of the plurality of cells. In one embodiment, the set of nuclear morphology features describe a shape of the cellular nucleus, a size of the cellular nucleus, and a texture of the cellular nucleus. In one embodiment, the set of nuclear morphology features includes six nuclear morphology features. Extracting the set of nuclear morphology features includes acquiring electronic data, reading from a computer file, receiving a computer file, reading from a computer memory, or other computerized activity not practically performed in a human mind.

The set of operations 500 also includes, at 550, constructing a feature driven local cell graph (FeDeG). The FeDeG is constructed based on the set of nuclear morphology features and a spatial relationship between the members of the plurality of cellular nuclei. In one embodiment, the FeDeG is constructed based on the set of nuclear morphology features extracted from the segmented nucleus of the first member of the plurality of cells, and the cellular nucleus of the at least one second, different member of the plurality of cells, respectively. The FeDeG is constructed using a mean-shift clustering approach. In one embodiment, the mean-shift clustering approach includes estimating the mode of an underlying density function of a member of the set of nuclear morphology features, and grouping a cellular nucleus of a member of the plurality of cells into a sub-graph based on the corresponding mode. Embodiments may construct a FeDeG or plurality of FeDeGs from all the members of the plurality of cells, or from a threshold number of the members of the plurality of cells. Constructing the FeDeG includes acquiring electronic data, reading from a computer file, receiving a computer file, reading from a computer memory, or other computerized activity not practically performed in a human mind.

The set of operations 500 also includes, at 560, computing a set of FeDeG features based on the FeDeG. In one embodiment, the set of FeDeG features includes four groups of features. The four groups of features include an intersection between different FeDeGs feature group; a size of FeDeG feature group; a disorder of nuclear morphology feature group; and an architectural measures of FeDeGs feature group. In one embodiment, the set of FeDeG features includes at least one feature selected from each of the four groups of features, respectively. Computing the set of FeDeG features includes acquiring electronic data, reading from a computer file, receiving a computer file, reading from a computer memory, or other computerized activity not practically performed in a human mind.

The set of operations 500 also includes, at 570, providing the set of FeDeG features to a machine learning classifier. In one embodiment, the machine learning classifier is a linear discriminant analysis (LDA) classifier. In another embodiment, the machine learning classifier may be another type of machine learning classifier, including a quadratic discriminant analysis (QDA) classifier, a support vector machine (SVM) classifier, or a random forests classifier. In another embodiment, the machine learning classifier may be a deep learning classifier, including, for example, a convolutional neural network (CNN).

The set of operations 500 also includes, at 580, receiving, from the machine learning classifier, a classification of the ROI as a long-term survivor or a short-term survivor. The machine learning classifier computes the classification based, at least in part, on the set of FeDeG features. Receiving the classification includes acquiring electronic data, reading from a computer file, receiving a computer file, reading from a computer memory, or other computerized activity not practically performed in a human mind.

The set of operations 500 further includes, at 590, displaying the classification. Displaying the classification may include displaying the classification on a computer monitor, a smartphone display, a tablet display, or other displays. Displaying the classification may also include printing the classification. Displaying the classification may also include controlling a cancer survival prediction system, a computer assisted diagnostic (CADx), system a monitor, or other display, to display operating parameters or characteristics of a machine learning classifier, during both training and testing, or during clinical operation of the machine learning classifier. By displaying the classification, example embodiments provide a timely and intuitive way for a human pathologist or other medical practitioner to more accurately predict overall survival in early stage lung cancer, thus improving on existing approaches to predicting overall survival. The set of operations may further include, at 590, displaying the image, the FeDeG, the set of nuclear morphology features, a segmented cellular nucleus, or the plurality of cells.

Figure 6:
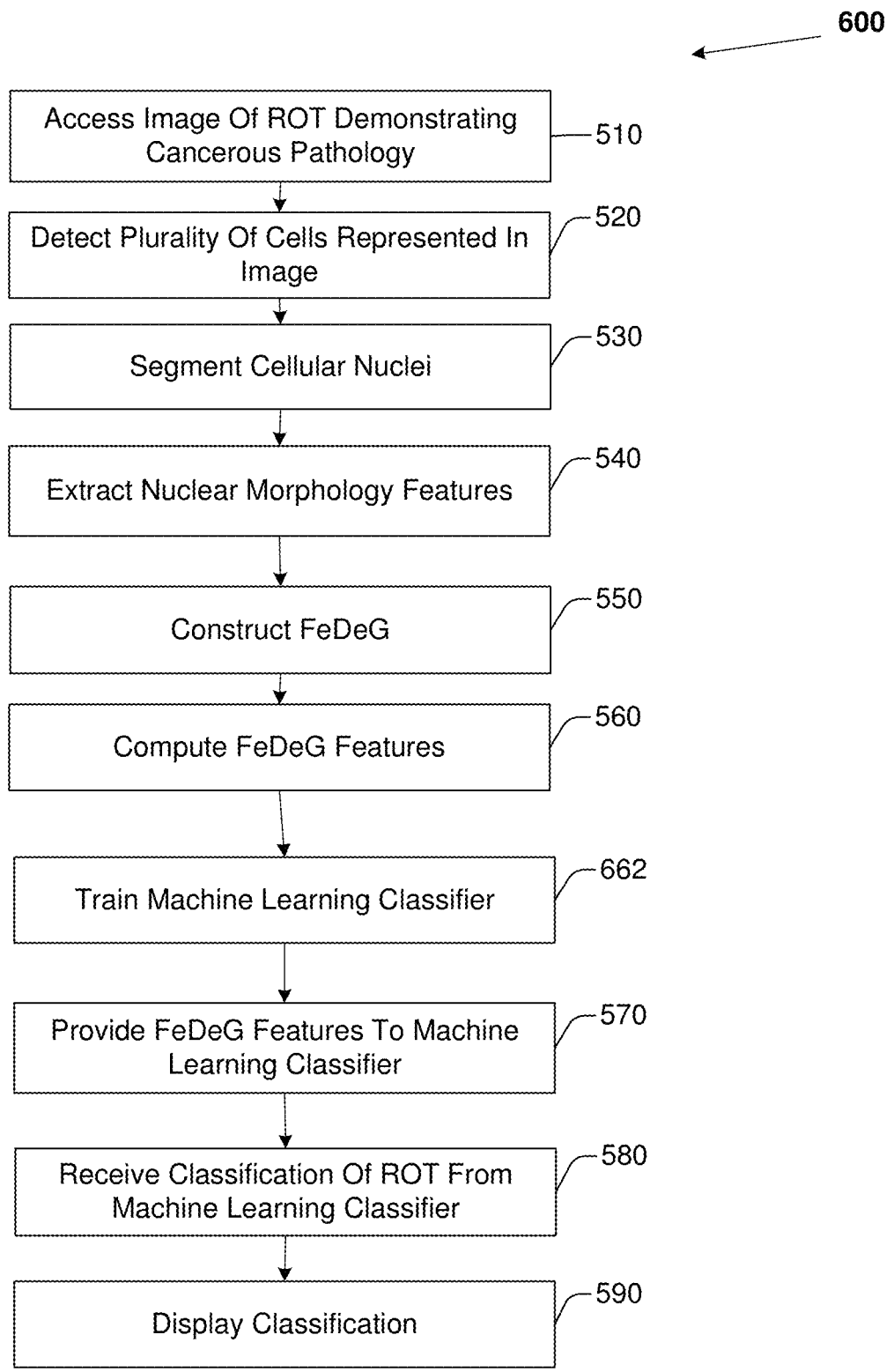
FIG. 6 is a flow diagram of example operations for predicting overall survival in NSCLC.

In one embodiment, the operations may further include training the machine learning classifier. FIG. 6 is a flow diagram of example operations 600 that is similar to operations 500 but that includes additional details and elements. In this embodiment, operations 600 include, at 662, training the machine learning classifier. The machine learning classifier is trained and tested using a training set of images and a testing set of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which nuclear morphology features or FeDeG features are most discriminative in distinguishing a positive class from a negative class (e.g., long-term survivor, short-term survivor).

While FIGS. 5 and 6 illustrate various actions occurring in serial, it is to be appreciated that various actions illustrated in FIG. 5 or FIG. 6 could occur substantially in parallel. By way of illustration, a first process could involve accessing an image of a region of tissue demonstrating NSCLC, a second process could involve segmenting a cellular nucleus, and a third process could involve extracting a set of nuclear morphology features from a segmented cellular nucleus. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including operations 500 or 600, method 1000, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved prediction of overall survival in NSCLC may produce the technical effect of improving the administration of NSCLC treatments, by increasing the accuracy of and decreasing the time required to determine if a patient is likely to experience long-term or short-term survival. Treatments and resources, including expensive immunotherapy agents or chemotherapy may be more accurately tailored to patients with a likelihood of benefiting from said treatments and resources, including responding to immunotherapy or chemotherapy, so that more appropriate treatment protocols may be employed, and expensive resources are not wasted, when digitized H&E images are more accurately and more quickly assessed for predicted overall survival. Controlling an NSCLC overall survival prediction apparatus, a CADx system, a personalized medicine system, or other apparatus configured to predict overall survival in NSCLC, based on improved, more accurate analysis of digitized H&E images further improves the operation of the system, processor, or apparatus, since the accuracy of the system, processor, or apparatus is increased and unnecessary operations will not be performed.

Embodiments described herein, including at least operations 500 and 600, apparatus 700 or 800, or method 1000, resolve features extracted from digitized H&E images imagery at a higher order or higher level than a human can resolve in the human mind or with pencil and paper. For example, nuclear morphological features that are not perceivable by the human eye may be detected by embodiments, and FeDeGs and FeDeG features generated by embodiments are not properties of a tissue slide that are perceivable by the human eye, computable using pencil and paper, or practically computed in the human mind. Embodiments thus perform actions, steps, processes, or other actions that are not practically performed in the human mind, at least because they require a processor or circuitry to access digitized images stored in a computer memory and to extract or compute features including the generation of FeDeGs and FeDeG features that are based on the digitized images and not on properties of tissue or the images that are perceivable by the human eye. Embodiments described herein use a combined order of specific rules, elements, operations, or components that render information into a specific format that is then used and applied to create desired results more accurately, more consistently, and with greater reliability than existing approaches, thereby producing at least the technical effect of improving the performance of the machine, computer, or system with which embodiments are implemented.

Figure 7:
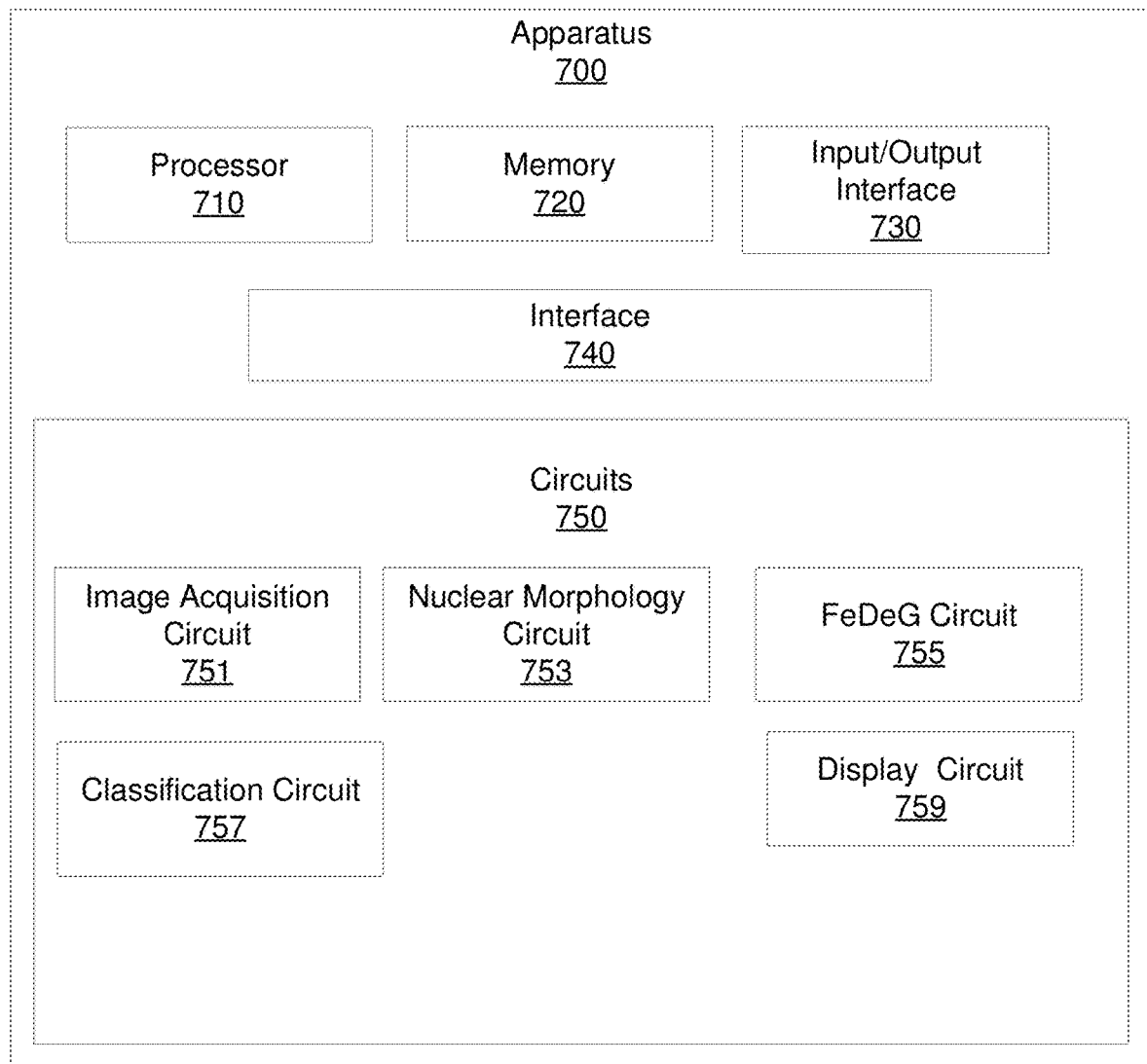
FIG. 7 illustrates an example apparatus for predicting overall survival in NSCLC.

FIG. 7 illustrates an example apparatus 700 for predicting overall survival in lung cancer patients. Apparatus 700 includes a processor 710. Apparatus 700 also includes a memory 720. Processor 710 may, in one embodiment, include circuitry such as, but not limited to, one or more single-core or multi-core processors. Processor 710 may include any combination of general-purpose processors and dedicated processors (e.g., graphics processors, application processors, etc.). The processors may be coupled with or may include memory (e.g. memory 720) or storage and may be configured to execute instructions stored in the memory 720 or storage to enable various apparatus, applications, or operating systems to perform the operations. Memory 720 is configured to store a digitized image of a region of tissue (ROT) demonstrating cancerous pathology. The digitized image has a plurality of pixels, a pixel having an intensity. Memory 720 may be further configured to store a training set of images demonstrating cancerous pathology, where at least one member of the training set is classified as long-term survivor, and at least one other, different member of the training set is classified as a short-term survivor, or a testing set of images demonstrating cancerous pathology, where at least one member of the testing set is classified as a long-term survivor, and at least one other, different member of the testing set is classified as a short-term survivor.

Apparatus 700 also includes an input/output (I/O) interface 730, a set of circuits 750, and an interface 740 that connects the processor 710, the memory 720, the I/O interface 730, and the set of circuits 750. I/O interface 730 may be configured to transfer data between memory 720, processor 710, circuits 750, and external devices, for example, a lung cancer overall survival prediction system, a CADx system, or a digital whole slide scanner.

The set of circuits 750 includes an image acquisition circuit 751. Image acquisition circuit 751 is configured to access a digitized image of an ROT demonstrating cancerous pathology. The digitized image has a plurality of pixels, a pixel having an intensity. In one embodiment the digitized image is a digitized H&E stained TMA image of a region of tissue demonstrating NSCLC scanned at 20× magnification.

In another embodiment, other types of image staining, or other magnification levels may be employed. Accessing the digitized image may include accessing a digitized image stored in memory 720. In one embodiment, accessing the digitized image may include accessing a digitized image stored in a data storage device, including a hard disk drive, a solid state device, a tape drive, or accessing a digitized image over a local area network or from the cloud. Accessing the digitized image includes acquiring electronic data, reading from a computer file, receiving a computer file, reading from a computer memory, or other computerized activity not practically performed in a human mind.

Image acquisition circuit 751 is also configured to detect a plurality of cells represented in the digitized image. A member of the plurality of cells includes a cellular nucleus. In one embodiment, image acquisition circuit 751 is configured to detect the plurality of cells represented in the digitized image using a multiple-pass adaptive voting approach. In another embodiment, image acquisition circuit 751 may be configured to detect the plurality of cells using another, different, detection technique. In another embodiment, the plurality of cells may be have been detected by, for example, another, different system or apparatus, prior to image acquisition circuit 751 accessing the digitized image.

The set of circuits 750 also includes a nuclear morphology circuit 753. Nuclear morphology circuit 753 is configured to, for each member of the plurality of cells: segment a cellular nucleus represented in the digitized image, respectively. In another embodiment, nuclear morphology circuit 753 is configured to, for each of a threshold number (e.g., 75%, 90%) of the members of the plurality of cells, where the threshold number is less than all the members of the plurality of cells: segment a cellular nucleus represented in the digitized image, respectively. In one embodiment, nuclear morphology circuit 753 is configured to segment a cellular nucleus using a local optimal thresholding approach. In another embodiment, nuclear morphology circuit 753 may be configured to segment a cellular nucleus using a different segmentation approach.

Nuclear morphology circuit 753 is also configured to, for each member of the plurality of cells, compute a set of nuclear morphology features based on the segmented cellular nucleus. In one embodiment, the set of nuclear morphology features includes at least six features. In another embodiment, the set of nuclear morphology features may include another, different number of features.

The set of circuits 750 also includes a feature driven local cell graph (FeDeG) circuit 755. FeDeG circuit 755 is configured to construct a FeDeG based on the segmented nuclei and the set of nuclear morphology features. FeDeG circuit 755 is configured to construct the FeDeG using a mean-shift clustering approach.

FeDeG circuit 755 is further configured to compute a set of FeDeG features based on the FeDeG. In one embodiment, the set of FeDeG features includes: at least one intersection between different FeDeGs feature; at least one size of FeDeG feature; at least one disorder of nuclear morphology feature; and at least one architectural measures of FeDeGs feature. In another embodiment, FeDeD circuit 755 may be configured to compute, other, different FeDeG features.

The set of circuits 750 also includes a classification circuit 757 configured to generate a classification of the ROT as a long-term survivor or short-term survivor. Classification circuit 757 is configured to generate the classification based on the set of FeDeG features. Classification circuit 757 may be configured to generate the classification based on the set of FeDeG features and the FeDeG. In one embodiment, classification circuit 757 is configured as a linear discriminant analysis (LDA) classifier. In another embodiment, classification circuit 757 may be configured as another, different type of machine learning classifier or deep learning classifier, including, for example, a QDA classifier, a random forests classifier, or as a CNN classifier.

The set of circuits 750 also includes a display circuit 759. Display circuit 759 is configured to display the classification. In one embodiment, display circuit 759 is further configured to display at least one of a FeDeG, the digitized image, or the set of FeDeG features. Displaying at the classification or at least one of a FeDeG, the digitized image, or the set of FeDeG features may also include printing the classification or at least one of the FeDeG, the digitized image, or the set of FeDeG features.

Figure 8:
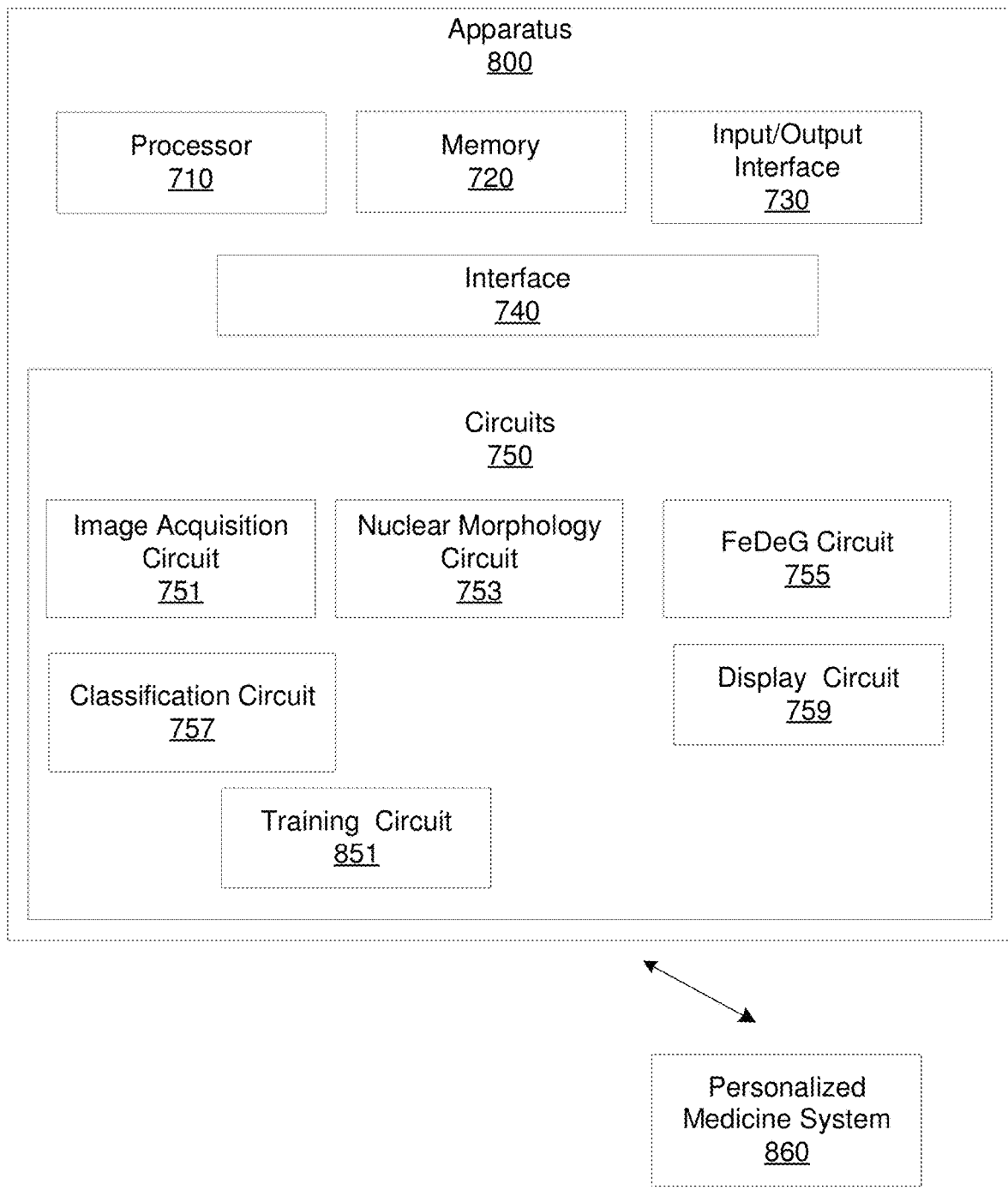
FIG. 8 illustrates an example apparatus for predicting overall survival in NSCLC.

In one embodiment, apparatus 700 may also include a training circuit. FIG. 8 illustrates an apparatus 800 that is similar to apparatus 700 but that includes additional details and features. Apparatus 800 includes training circuit 851. The training circuit 851 may be configured to train a machine learning classifier (e.g., classification circuit 757) to classify a digitized image of a region of tissue demonstrating NSCLC according to techniques described herein. In one embodiment, training circuit 851 is configured to access a training dataset of digitized images. The training circuit 851 may be further configured to access a testing dataset of digitized images. At least one member of the training set is classified as a long-term survivor, and at least one other, different member of the training set is classified as a short-term survivor. At least one member of the testing set is classified as a long-term survivor, and at least one other, different member of the testing set is classified as a short-term survivor. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

FIG. 8 also illustrates a personalized medicine system 860. Apparatus 800 may be configured to transmit at least one of the classification, a FeDeG, the digitized image, or the set of FeDeG features to the personalized medicine system 860. Personalized medicine system 860 may be, for example, a CADx system, an early stage NSCLC overall survival prediction system, or other type of personalized medicine device that may be used to facilitate the classification of tissue. In one embodiment, apparatus 800 may control personalized medicine system 860 to display the classification, a FeDeG, the digitized image, or the set of FeDeG features on a computer monitor, a smartphone display, a tablet display, or other displays.

Figure 9:
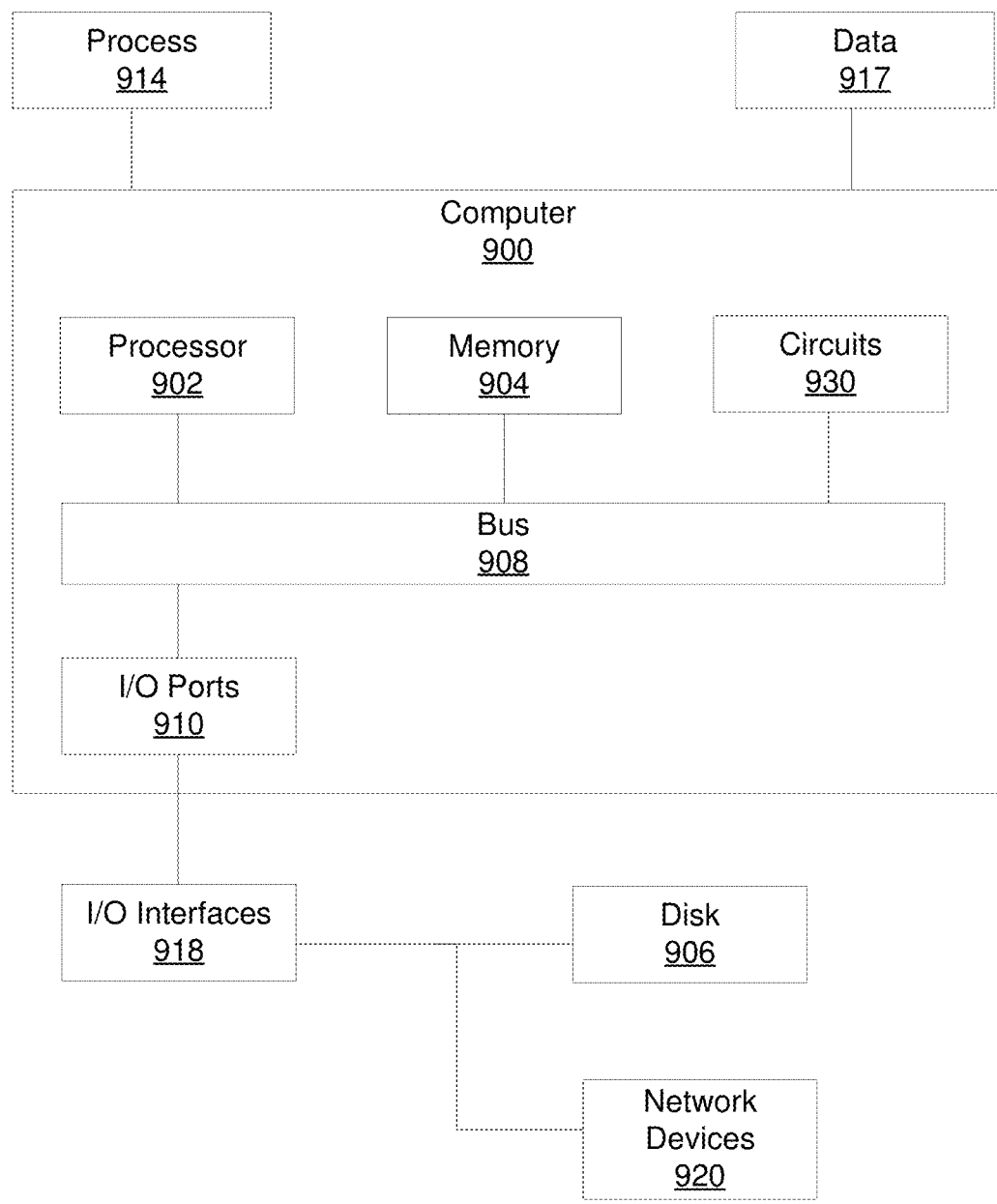
FIG. 9 illustrates an example computer in which embodiments described herein may operate.

FIG. 9 illustrates an example computer 900 in which example methods illustrated herein can operate and in which example methods, apparatus, circuits, operations, or logics may be implemented. In different examples, computer 900 may be part of a NSCLC overall survival prediction system or apparatus, a CADx system, a digital whole slide scanner, or a personalized medicine system, may be operably connectable to a NSCLC overall survival prediction system or apparatus, a personalized medicine system, or a digital whole slide scanner.

Computer 900 includes a processor 902, a memory 904, and input/output (I/O) ports 910 operably connected by a bus 908. In one example, computer 900 may include a set of logics or circuits 930 that perform operations for or a method of predicting overall survival in NSCLC, including by using a machine learning classifier. Thus, the set of circuits 930, whether implemented in computer 900 as hardware, firmware, software, and/or a combination thereof may provide means (e.g., hardware, firmware, circuits) for predicting overall survival in NSCLC. In different examples, the set of circuits 930 may be permanently and/or removably attached to computer 900.

Processor 902 can be a variety of various processors including dual microprocessor and other multi-processor architectures. Processor 902 may be configured to perform steps of methods claimed and described herein. Memory 904 can include volatile memory and/or non-volatile memory. A disk 906 may be operably connected to computer 900 via, for example, an input/output interface (e.g., card, device) 918 and an input/output port 910. Disk 906 may include, but is not limited to, devices like a magnetic disk drive, a tape drive, a Zip drive, a flash memory card, or a memory stick. Furthermore, disk 906 may include optical drives like a CD-ROM or a digital video ROM drive (DVD ROM). Memory 904 can store processes 914 or data 917, for example. Data 917 may, in one embodiment, include digitized H&E images. Disk 906 or memory 904 can store an operating system that controls and allocates resources of computer 900.

Bus 908 can be a single internal bus interconnect architecture or other bus or mesh architectures. While a single bus is illustrated, it is to be appreciated that computer 900 may communicate with various devices, circuits, logics, and peripherals using other buses that are not illustrated (e.g., PCIE, SATA, Infiniband, 794, USB, Ethernet).

Computer 900 may interact with input/output devices via I/O interfaces 918 and input/output ports 910. Input/output devices can include, but are not limited to, CT systems, MRI systems, digital whole slide scanners, an optical microscope, a keyboard, a microphone, a pointing and selection device, cameras, video cards, displays, disk 906, network devices 920, or other devices. Input/output ports 910 can include but are not limited to, serial ports, parallel ports, or USB ports.

Computer 900 may operate in a network environment and thus may be connected to network devices 920 via I/O interfaces 918 or I/O ports 910. Through the network devices 920, computer 900 may interact with a network. Through the network, computer 900 may be logically connected to remote computers. The networks with which computer 900 may interact include, but are not limited to, a local area network (LAN), a wide area network (WAN), or other networks, including the cloud.

Figure 10:
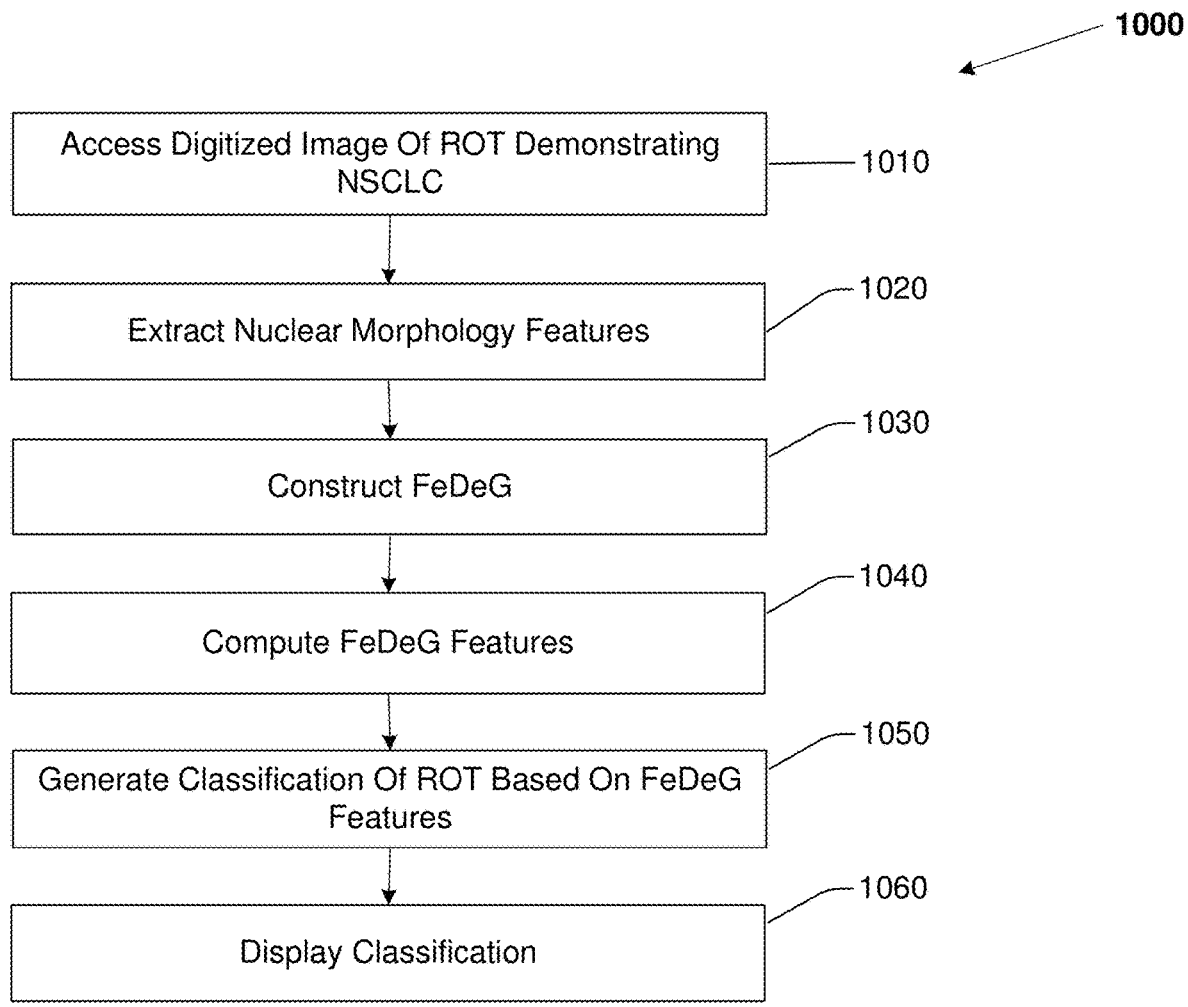
FIG. 10 illustrates an example method for predicting overall survival in NSCLC.

FIG. 10 illustrates an example method 1000. Method 1000 includes, at 1010 accessing a digitized image of a region of tissue (ROT) demonstrating non-small cell lung cancer (NSCLC). The ROT includes a plurality of cellular nuclei. The digitized image has a plurality of pixels, a pixel having an intensity. Accessing the digitized image includes acquiring electronic data, reading from a computer file, receiving a computer file, reading from a computer memory, or other computerized activity not practically performed in a human mind.

Method 1000 also includes, at 1020, extracting a set of nuclear morphology features from a member of the plurality of cellular nuclei. The set of nuclear morphology features including at least six features. Extracting the set of nuclear morphology features includes acquiring electronic data, reading from a computer file, receiving a computer file, reading from a computer memory, or other computerized activity not practically performed in a human mind.

Method 1000 also includes, at 1030, constructing a feature driven local cell graph (FeDeG). The FeDeG is constructed based on the plurality of cellular nuclei and the set of nuclear morphology features associated with each nucleus, respectively. The FeDeG is constructed using a mean-shift clustering approach. Constructing the FeDeG includes acquiring electronic data, reading from a computer file, receiving a computer file, reading from a computer memory, or other computerized activity not practically performed in a human mind.

Method 1000 also includes, at 1040, computing a set of FeDeG features based on the FeDeG. The set of FeDeG features includes at least one intersection between different FeDeGs feature, at least one size of FeDeG feature, at least one disorder of nuclear morphology feature, and at least one architectural measures of FeDeGs feature. Computing the set of FeDeG features includes acquiring electronic data, reading from a computer file, receiving a computer file, reading from a computer memory, or other computerized activity not practically performed in a human mind.

Method 1000 also includes, at 1050, generating a classification of the ROT as a short-term survivor or long-term survivor based on a linear discriminant analysis of the set of FeDeG features. In one embodiment, generating the classification includes providing the set of FeDeG features to an LDA classifier, and receiving, from the LDA classifier, a classification of the ROT as a short-term survivor or long-term survivor. The LDA classifier computes the classification based on the set of FeDeG features. Generating the classification includes acquiring electronic data, reading from a computer file, receiving a computer file, reading from a computer memory, or other computerized activity not practically performed in a human mind.

Method 1000 also includes, at 1060, displaying the classification. Displaying the classification may include displaying the classification on a computer monitor, a smartphone display, a tablet display, or other displays. Displaying the classification may also include printing the classification. In one embodiment, method 1000 further includes, at 1060, displaying at least one of the digitized image, the set of nuclear morphology features, the FeDeG, or the set of FeDeG features.

Examples herein can include subject matter such as an apparatus, an NSCLC overall survival prediction system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting overall survival in NSCLC, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed control a processor to perform operations, the operations comprising:

accessing an image of a region of tissue demonstrating a disease, and containing a plurality of cellular structures, at least some of the plurality of cellular structures being of different types;

for each cellular structure of a subset of the plurality of cellular structures, extracting one or more cell structure-level features from that cellular structure, at least some of the one or more cell structure-level features being indicative of the different types;

constructing one or more graphs, wherein each of the one or more graphs is based on both (a) the one or more cell structure-level features, and (b) one or more spatial relationships between at least one cellular structure of the subset and one or more other cellular structures of the subset, the one or more cell structure-level features and the one or more spatial relationships being independent of one another, such that said constructing differentiates between the different types of the plurality of cellular structures;

computing one or more graph-level features based on the one or more graphs; and generating a medical prediction related to the disease based, at least in part, on the one or more graph-level features.

2. The non-transitory computer-readable storage device of claim 1, where the image is a digitized image of a hematoxylin and eosin (H&E) stained tissue micro array (TMA) image of a region of tissue demonstrating non-small cell lung cancer (NSCLC).

3. The non-transitory computer-readable storage device of claim 2, where the image is scanned at 20× magnification.

4. The non-transitory computer-readable storage device of claim 1, wherein the one or more graph-level features describe a topology or a heterogeneity of constituent cell structures of the one or more graphs.

5. The non-transitory computer-readable storage device of claim 1, wherein the plurality of cellular structures comprise entire cells, cellular nuclei, or both.

6. The non-transitory computer-readable storage device of claim 1, the operations further comprising segmenting one or more cellular structures of the plurality of cellular structures using a local optimal thresholding approach, where the local optimal thresholding approach is based on a cellular shape of that cellular structure, and a cellular area of that cellular structure.

7. The non-transitory computer-readable storage device of claim 1, where the one or more cell structure-level features describe a shape of that cellular structure, a size of that cellular structure, and a texture of that cellular structure.

8. The non-transitory computer-readable storage device of claim 7, where the one or more cell structure-level features include six nuclear morphology features.

9. The non-transitory computer-readable storage device of claim 1, where constructing the one or more graphs comprises using a mean-shift clustering approach that includes:

estimating a mode of an underlying density function of a member of the one or more cell structure-level features; and grouping a cellular structure of the plurality of cellular structures into a sub-graph based on the mode.

10. The non-transitory computer-readable storage device of claim 1, where the one or more graph-level features include four groups of features, the four groups of features including:

an intersection between different graph-level feature group;

a size of graph-level feature group;

a disorder of nuclear morphology feature group; and an architectural measure of graph-level feature group.

11. The non-transitory computer-readable storage device of claim 10, where the one or more graph-level features include at least one feature selected from each of the four groups of features, respectively.

12. The non-transitory computer-readable storage device of claim 1, the operations further comprising generating the medical prediction using a machine learning classifier, where the machine learning classifier is a linear discriminant analysis (LDA) classifier.

13. The non-transitory computer-readable storage device of claim 12, the operations further comprising training the machine learning classifier.

14. An apparatus comprising one or more processors configured to:

receive a digitized image of a region of tissue (ROT) demonstrating a disease and containing a plurality of cellular structures, at least some of the plurality of cellular structures being of different types;

for each cellular structure of a subset of the plurality of cellular structures, compute one or more cell structure-level features based on that cellular structure, at least some of the one or more cell structure-level features being indicative of the different types;

construct one or more graphs, wherein each of the one or more graphs is based on both (a) the one or more cell structure-level features, and (b) one or more spatial relationships between at least one cellular structure of the subset and one or more other cellular structures of the subset, the one or more cell structure-level features and the one or more spatial relationships being independent of one another, such that said constructing differentiates between the different types of the plurality of cellular structures;

compute one or more graph-level features based on the one or more graphs; and generate a medical prediction related to the disease based, at least in part, on the one or more graph-level features.

15. The apparatus of claim 14, where the digitized image is a digitized hematoxylin and eosin (H&E) stained tissue micro array (TMA) image of a region of tissue demonstrating non-small cell lung cancer (NSCLC) scanned at 20× magnification.

16. The apparatus of claim 14, wherein the one or more processors are further configured to detect the plurality of cellular structures of the digitized image using a multiple-pass adaptive voting approach.

17. The apparatus of claim 14, wherein the one or more processors are further configured to, for each cellular structure of the plurality of cellular structures, segment that cellular structure using a local optimal thresholding approach.

18. The apparatus of claim 14, where the one or more graph-level features include:

at least one intersection between different graph-level feature;

at least one size of graph-level feature;

at least one disorder of nuclear morphology feature; and at least one architectural measure of graph-level feature.

19. The apparatus of claim 14, wherein the one or more processors are further configured to generate the medical prediction using a linear discriminant analysis (LDA) classifier.

20. A method comprising:
- accessing an image of a region of tissue demonstrating a disease, and containing a plurality of cellular structures, at least some of the plurality of cellular structures being of different types;
- for each cellular structure of a subset of the plurality of cellular structures, extracting one or more cell structure-level features from that cellular structure, at least some of the one or more cell structure-level features being indicative of the different types;
- constructing one or more graphs, wherein each of the one or more graphs is based on both (a) the one or more cell structure-level features, and (b) one or more spatial relationships between at least one cellular structure of the subset and one or more other cellular structures of the subset, the one or more cell structure-level features and the one or more spatial relationships being independent of one another, such that said constructing differentiates between the different types of the plurality of cellular structures;
- computing one or more graph-level features based on the one or more graphs; and
- generating a medical prediction related to the disease based, at least in part, on the one or more graph-level features.

* * * * *